United States Patent [19]

Nishimura et al.

[11] Patent Number: 4,983,747

[45] Date of Patent: Jan. 8, 1991

[54] PROCESS FOR PREPARATION OF PERFLUORO ORGANIC COMPOUNDS

[75] Inventors: Masakatsu Nishimura, Tokuyama; Naoya Okada, Nanyo; Yasuo Murata, Kudamatsu; Yasuhiko Hirai, Tokuyama, all of Japan

[73] Assignee: Tokuyama Soda Kabushiki Kaisha, Yamaguchi, Japan

[21] Appl. No.: 493,803

[22] Filed: Mar. 15, 1990

Related U.S. Application Data

[62] Division of Ser. No. 127,115, Dec. 1, 1987, Pat. No. 4,929,317.

[30] Foreign Application Priority Data

Dec. 1, 1986 [JP] Japan ................................. 61-284260
Dec. 1, 1986 [JP] Japan ................................. 61-284261

[51] Int. Cl.$^5$ ................................. C07C 309/08
[52] U.S. Cl. ................................. 549/423; 260/408; 560/227; 562/113; 562/603; 562/825; 564/183; 564/412; 564/496; 568/406; 568/842; 570/123; 570/147
[58] Field of Search ................ 570/123, 147; 568/408, 568/842; 564/183, 412, 496; 562/113, 603, 825; 560/227, 408; 549/423; 260/408

[56] References Cited

U.S. PATENT DOCUMENTS 2,519,983 8/1950 Simons ................................. 204/62

FOREIGN PATENT DOCUMENTS 0121614 10/1984 European Pat. Off. .
60-202122 10/1985 Japan .

OTHER PUBLICATIONS

Lin et al., "The First Perfluoro Crown Ethers", J. Chem. SOC. Chem. Commun., 1985 (19), pp. 1350-1352.

Gervasi et al., "The Action of Elementary ... Ethylenediamine and Ethyleneimine", J. Am. Chem. Soc., 1956, 78, pp. 1679-1682.

Persico et al., "Synthesis of Perfluoropolyethers via Hydrocarbon Polyesters: A New General Method", J. Am. Chem. Soc., 1985, 107(5), pp. 1197-1201.

Hudlicky, "Chemistry of Organic Fluorine Compounds", 2nd Edition (1976), Published by Ellis Horwood Limited, pp. 77-82.

Primary Examiner—Richard L. Raymond
Attorney, Agent, or Firm—Sherman and Shalloway

[57] ABSTRACT

Disclosed is a process for the preparation of a perfluoroorganic compound, which comprises fluorinating a partially fluorinated or unfluorinated organic compound having carbon-to-fluorine bonds under mild conditions and then, contacting the resulting reaction mixture with a fluorine gas at a temperature of 110° to 180° C.

1 Claim, No Drawings

PROCESS FOR PREPARATION OF PERFLUORO ORGANIC COMPOUNDS

This is a division of application Ser. No. 127,115, filed Dec. 1, 1987, now U.S. Pat. No. 4,929,317.

BACKGROUND OF THE INVENTION (1) Field of the Invention

The present invention relates to a process for the preparation of perfluoro organic compounds.

(2) Description of the Related Art

In general, perfluoro organic compounds are chemically stable, have a high insulating strength, a high heat conductivity, a small surface tension and a high oxygen-dissolving power and is uncombustible, nontoxic and odorless. Because of these good characteristics, these compounds have been used as test bath media for electronic parts, heat media for the gas-phase soldering, insulating coolants for electronic appliances, oxygen carriers for artificial blood and operating fluids for heat pipes.

These perfluoro organic compounds are generally linear or cyclic perfluorocarbon compounds containing or not containing such atoms as nitrogen, oxygen and sulfur in the molecules.

In the instant specification and appended claims, perfluorocarbon compounds containing or not containing such atoms are inclusively called "perfluoro organic compounds".

Perfluoro organic compounds are prepared by substituting hydrogen atoms of an unfluorinated or partially fluorinated, saturated or unsaturated organic compound having a certain skeleton with fluorine atoms and/or adding fluorine atoms to this organic compound The fluorinating means adopted in this preparation process is roughly divided into (i) a method using a fluorine gas, such as disclosed in Japanese Patent Application Laid-Open Specification No. 202122/85, J. Chem. Soc. Chem. Commun., 1985(19), 1350-2, J. Am. Chem. Soc., 1956, 78, 1679-82 or J. Am. Chem. Soc., 1985, 107(5), 1197-201, (ii) a method using a fluoride of a metal of a high atomic valency, such as disclosed in "Chemistry of Organic Fluorine Compounds", 2nd edition (1976), written by Milos Hudlicky and published by Ellis Horwood Limited, pages 77-82, and (iii) a method of electrochemical fluorination in HF, such as disclosed in the specification of U.S. Pat. No. 2,519,983 or the specification of European Patent No. 121,614.

In the fluorination method (i) using a fluorine gas, the reaction is generally violent. Accordingly, in many cases the liquid-phase reaction is carried out under such severe conditions that the temperature is controlled below 0° C. and the reaction mixture is diluted, or the method (i) is used for partial fluorination for partial introduction of fluorine. If it is intended to effect complete substitution of hydrogen atoms in an organic compound having carbon-to-hydrogen bonds by using a fluorine gas, side reactions such as cleavage of the molecule and decomposition of functional groups are easily caused, and especially in case of amine compounds or the like, the yield is often drastically reduced.

In the fluorination method (ii) using a fluoride of a metal of a high atomic valency, such as cobalt trifluoride, a by-product is easily formed by decomposition, though not so conspicuous as in the method (i), and if complete fluorination is intended, drastic reduction of the yield is caused.

The electrochemical fluorination method (iii) is relatively simple. However, according to this method, the conversion to a perfluoro organic compound is fundamentally low, and it has been confirmed by us that when the formed perfluoro organic compound is separated in the form of a precipitate or gas from the electrolysis system, incompletely fluorinated compounds, for example, compounds having one or two hydrogen atoms in the molecule, are included in unexpectedly large amounts in the precipitate or gas. This phenomenon is especially conspicuous when the perfluoro organic compound is recovered in the form of precipitate.

In the case where a perfluoro compound is applied to the above-mentioned uses, an incompletely fluorinated compound as described above causes serious troubles even if the amount incorporated of the incompletely fluorinated compound is very small. For example, when the perfluoro organic compound is used as an oxygen carrier for artificial blood, because of the toxicity of the incompletely fluorinated compound to the living body, it is necessary to remove the incompletely fluorinated compound completely. As means for removing the incompletely fluorinated compound, there are known some method in which the fluorination product is treated for example with an alkali metal or alkaline earth metal. However, if these methods are adopted, the loss of the perfluoro organic compound cannot be avoided, and a problem of reduction of the yield arises.

SUMMARY OF THE INVENTION

It is therefore a primary object of the present invention to provide a process in which a perfluoro organic compound having a high purity is easily prepared in a high yield.

More specifically, in accordance with the present invention, there is provided a process for the preparation of perfluoro organic compounds by perfluorination of organic compounds having carbon-to-hydrogen bonds, which comprises the first step of gently fluorinating an organic compound having carbon-to-hydrogen bonds to form a mixture of compounds in which the ratio of the number of fluorine atoms to the number of hydrogen atoms is at least 8, and the second step of contacting said mixture with molecular fluorine temperature of 110° to 180° C.

DETAILED DESCRIPTION OF THE PREFERRED EMBODIMENTS

At the first step of the process of the present invention, a starting organic compound having carbon-to-hydrogen bonds is subjected to gentle fluorination. As this gentle fluorination, there can be mentioned electrochemical fluorination, fluorination using a fluoride of a metal of a high valency, and fluorination by reacting the starting organic compound with a fluorine gas at a low temperature, for example, a temperature lower than 20° C.

As pointed out hereinbefore, considerable amounts of incompletely fluorinated compounds are contained in the product formed by this gentle fluorination, especially electrochemical fluorination, and it is difficult to obtain a perfluoro organic compound at a high purity.

However, it is generally possible to substitute a major part of hydrogen atoms of the starting organic compound with fluorine atoms by the gentle fluorination, and if the reaction is carried out in an appropriate manner, it is possible to convert at least a half of the organic compound to the intended perfluoro organic compound.

Accordingly, at the first step of the process of the present invention, a starting organic compound having carbon-to-hydrogen atoms is subjected to gentle fluorination to substitute hydrogen atoms of the organic compound with fluorine atoms, whereby a mixture of the intended perfluoro organic compound and a partially fluorinated compound. At this first step, the gentle fluorination is carried out so that in the partially fluorinated organic compound, the ratio of the number of introduced fluorine atoms to the number of remaining hydrogen atoms (hereinafter referred to as "F/H ratio") is at least 8/1, preferably at least 10/1. Although the upper limit of the F/H ratio is not particularly critical, at least one hydrogen atom is left in the partially fluorinated organic compound, and in the case where the number of carbon atoms in the starting organic compound is large, for example, 30 or more, the F/H ratio is up to 60/1, preferably up to 50/1. From the results of experiments made by us, it was confirmed that if the F/H ratio is smaller than 8/1, at the second step described hereinafter, a side reaction is easily caused or only a perfluoro organic compound containing a large amount of an incompletely fluorinated compound is obtained.

At the second step of the process of the present invention, the reaction mixture obtained at the first step is treated with a fluorine gas at a temperature of 110° to 180° C., preferably 120° to 150° C.

The temperature is an important factor for the reaction of the second step of the process of the present invention. If the temperature is lower than 110° C., it is almost impossible to perfluorinate the partially fluorinated organic compound obtained at the first step. If the temperature is higher than 180° C., a side reaction becomes vigorous, and it is therefore impossible to obtain the intended perfluoro organic compound in a high yield.

Of course, the reaction of the second step of the process of the present invention can be promoted by using a known catalyst, for example, a metal catalyst such as cobalt, nickel, brass, silver, gold or copper, or by irradiation with rays having a wave length of 200 to 600 nm.

The perfluoro organic compound obtained at the second step of the process of the present invention can be directly used according to circumstances, but the purity can be further improved by an alkali treatment, a rectification treatment or the like. When a high-purity perfluoro organic compound is desired, for example, a perfluoro organic compound for artificial blood, is desired, the obtained perfluoro organic compound should of course be purified.

The process of the present invention will now be described more specifically.

The starting organic compound used in the process of the present invention is a linear or cyclic aliphatic or aromatic compound having carbon-to-hydrogen bonds. This organic compound having carbon-to-hydrogen bonds has generally 4 to 24 carbon atoms, preferably 10 to 18 carbon atoms, which may contain other atoms such as halogens, nitrogen, oxygen and sulfur in the molecule. Namely, the starting organic compound used in the present invention includes (poly)ethers, amines, alcohols, amides, carboxylic acids, sulfonic acids, acid halides, esters and ketones. As specific examples, there can be mentioned octane, phenanthrene, decalin, caproyl chloride, octanesulfonyl chloride, tetrahydropyran, octyl alcohol, hexyl alcohol, octunoic acid, hexanoic acid, octanesulfonic acid, methyl octanoate, benzamide, 2-octanone, monohexylamine, dihexylamine, trihexylamine, tripropylamine, tributylamine, tripentylamine, trihexylamine, dipentylbutylamine and dibutylpropylamine.

Among these organic compounds, primary, secondary and tertiary amines are preferably fluorinated according to the process of the present invention, because a side reaction is easily caused when these amines are fluorinated according to the conventional techniques. Trialkylamines having 4 to 24 carbon atoms, particularly 10 to 18 carbon atoms, are especially preferably fluorinated according to the process of the present invention.

Of course, an organic compound in which hydrogen atoms are partially substituted with fluorine atoms may be used as the starting organic compound in the present invention. In this partially fluorinated organic compound, the F/H ratio should be smaller than 8.

The means for the gentle fluorination at the first step of the present invention is not particularly critical, but any of known methods can be adopted. However, in view of the simplicity of the means and the control of a side reaction, electrochemical fluorination in anhydrous hydrogen fluoride is especially preferred. According to this method, hydrogen fluoride and the starting organic compound are supplied to an electrolytic cell provided with an anode and a cathode, and electricity is applied between the both electrodes. Nickel or a nickel alloy is generally used for the anode, and nickel, a nickel alloy, iron, stainless steel or copper is generally used for the cathode. The electrolytic cell may be formed of the same material as that of the cathode or a fluororesin. It is preferred that the distance between the anode and the cathode electrodes be about 0.5 to about 5 mm.

The starting organic compound and hydrogen fluoride are supplied separately or in the mixed state into the electrolytic cell, and it is preferred that the ratio between the supplied organic compound and hydrogen fluoride be selected so that the concentration of the organic compound is 1 to 40% by weight in the electrolytic cell.

Known electrolysis conditions can be appropriately selected and adopted. In general, the temperature is $-15°$ to 20° C., the current density is 0.1 to 5 A/dm$^2$ and the cell voltage is 4 to 9 V. In order to improve the current density and stabilize the cell voltage, it is generally preferred that the electrolytic bath be stirred or circulated or an inert gas be blown into the bath.

The product is dense and insoluble in the bath liquid and is separated, precipitated and deposited from the bath liquid for the electrochemical fluorination and is obtained in the form of a mixture.

In the case where the molecular weight of the product is low, it sometimes happens that the product is discharged in the gaseous state from the electrolytic cell. In this case, the product is recovered by cooling the gas.

The product obtained by the electrochemical fluorination is ordinarily a perfluoro compound corresponding to the starting organic compound. For example, in the case where an alcohol is used, a perfluorocarboxylic acid fluoride or perfluorocarbon having the same carbon number as that of the starting alcohol is obtained. In the case where a carboxylic acid or carboxylic acid halide is used as tho starting organic compound, a perfluorocarboxylic acid fluoride having the same carbon number as that of the starting compound or a perfluorocarbon having a carbon number smaller by 1 than the carbon number of the starting compound is obtained. In this case, if the starting compound has a carbon number of 6 or more, a perfluoro cyclic ether having the same carbon number is obtained. A perfluorocarboxylic acid fluoride also is obtained from a carboxylic acid derivative such as an ester or an acid anhydride. From a sulfonic acid, a perfluorocarbon having the same carbon number is also obtained, and sulfonic acid chloride or sulfonic acid fluoride is used as the starting organic compound for perfluorosulfonic acid fluoride.

Another method to be adopted for the reaction of the first step is a fluorination method using a fluoride of a metal of a high valency.

In this method, cobalt trifluoride, potassium tetrafluorocobaltate, silver difluoride, manganese trifluoride, cerium tetrafluoride and lead tetrafluoride can be used as the fluoride of a metal of a high valency, and among these fluorides, cobalt trifluoride, potassium tetrafluorocobaltate, silver difluoride and manganese trifluoride are preferred.

The reaction between the fluoride of the high-valency metal and the starting organic compound such as a trialkylamine can be carried out in either the liquid phase or the gaseous phase. In case of the liquid-phase reaction, the reaction mixture is sufficiently stirred, and a diluting solvent or dispersant stable to the fluoride of the high-valency metal is ordinarily used to adjust the reaction temperature. The gas-phase reaction is generally preferable because the fluorination reaction is smoothly advanced. The starting organic compound is supplied to a reaction vessel singly or together with a gas inert to the fluoride of the high-valency metal, such as nitrogen or helium. In order to attain good contact between the starting organic compound and the fluoride of the high-valency metal, it is preferred that the fluoride of the high-valency be expanded in the form of a thin layer in the reaction vessel or be stirred. The reaction temperature is ordinarily in the range of from 100° to 400° C. The valency of the fluoride of the high-valency metal is reduced by the reaction. When the fluorinating capacity of the fluoride is reduced by this reduction of the valency, the metal fluoride can be regenerated by reacting it with a fluorine gas at a high temperature. Generally, the fluorination product and hydrogen fluoride formed as a by-product are separated from the inert gas and collected by a low-temperature trap. Subsequently to the gentle fluorination, hydrogen fluoride is removed by neutralization or the like according to need, and the product can be separated and purified by distillation or the like.

After the gentle fluorination conducted according to the above-mentioned method or other known method, the reaction of the second step of the process of the present invention is carried out.

The reaction mixture obtained at the preceding first step is directly used at the second step, but if the target perfluoro organic compound is additionally incorporated into this reaction mixture and the reaction is carried out in the more diluted state, the fluorination efficiency at the second step can be improved in the case.

At the second step, the mixture of the perfluoro organic compound and the partially fluorinated compound in which the F/H ratio is at least 8 is fluorinated. Preferably, the starting mixture comprises 100 parts by weight of the partially fluorinated organic compound and 40 to 600 parts by weight, particularly 70 to 500 parts by weight, especially particularly 100 to 400 parts by weight, of the intended perfluoro organic compound.

The fluorination using a fluorine gas at the second step is carried out according to known procedures by using a known apparatus except that the reaction temperature is controlled to 110° to 180° C. For example, the known liquid-gas or gas-gas reaction system can be adopted without any particular limitation.

At the second step, it is preferred that the starting mixture be contacted with the fluorine gas promptly and uniformly. This can be accomplished by the following methods:

(1) The fluorine gas is introduced into the starting mixture being stirred.
(2) The fluorine gas is introduced as bubbles into the liquid phase of the starting mixture.
(3) The liquid phase of the starting mixture is contacted in a counter-current manner with the fluorine gas (liquid phase absorption column system).
(4) The starting mixture is sprayed or dropped into the fluorine gas to effect contact between them (gas phase absorption column system).

In order to enhance the reaction efficiency by enhancing the contact efficiency, it is preferred that particles of nickel, a nickel alloy or other metal, a Raschig ring or a metal net be used as a filler.

The fluorine gas should be used in an amount larger than the theoretical amount necessary for substituting all of hydrogen atoms contained in the partially fluorinated organic compound in the starting mixture with fluorine atoms. For example, the fluorine gas is used in an amount about 1.1 to about 6 times the above-mentioned theoretical amount.

Pure fluorine gas (100% $F_2$) or a diluted fluorine gas containing at least 5% by volume, preferably 10 to 70% by volume, of $F_2$ is generally used as the fluorine gas.

In accordance with one preferred embodiment of the present invention, there is adopted a counter-current contact system in which the starting mixture is supplied from the column head, a fluorine gas having a high concentration, for example, 70 to 100% by volume, is introduced from the column bottom, and a diluent gas is introduced from the middle portion of the column to dilute the fluorine gas to a concentration of at least 5% by volume, whereby occurrence of the side reaction is effectively controlled. As the diluent gas, there can be used inert gases such as nitrogen, helium and neon.

A reaction pressure almost equal to the atmospheric pressure is sufficient, but an elevated pressure can be adopted. In view of the fluorination rate and the yield of the target perfluoro organic compound, it is preferred that the reaction temperature be 110° to 180° C., especially 120° to 150° C. The reaction time is not particularly critical, but generally, the reaction time is 1 to 30 hours. A particle or net of copper or a copper particle or net plated with silver may be used as the catalyst. Furthermore, the fluorination reaction can be promoted by irradiation with rays having a wavelength of 200 to 600 nm.

After the fluorination reaction using the fluorine gas, neutralization or distillation is carried out so as to remove hydrogen fluoride contained in the obtained product or increase the purity of the intended perfluoro organic compound.

The present invention will now be described in detail with reference to the following examples that by no means limit the scope of the invention.

EXAMPLE 1

Electrochemical fluorination of three amines shown in Table 1 was carried out by using an electrolytic cell formed of a fluororesin, which had a reflux cooler ($-40°$ C.) arranged in the upper portion thereof. The inner diameter of the electrolytic cell was 11 cm and the height was 25 cm. The cathode and the anode comprised 14 nickel plates (65 mm×96 mm and 1 mm in thickness) which were alternately arranged so that the distance between every two adjacent plates was 1.3 mm. The effective electrode area of the anode and cathode was 8 $dm^2$, respectively.

More specifically, 1500 g of anhydrous hydrogen fluoride and 150 g of the amine were supplied into the electrolytic cell, and electricity was applied under conditions shown in Table 1 until the starting amine was consumed and the cell voltage abruptly increased. Incidentally, the electrolysis temperature was kept constant by adjusting the temperature of a cooling medium for cooling the electrolytic cell. Then, the fluorination product deposited in the bottom portion of the electrolytic cell was withdrawn and the contained hydrogen fluoride was neutralized, and the fluorination product was washed with water and dried.

The amount and composition of the obtained fluorination product are shown in Table 1.

The analysis was carried out by the gas chromatography, the gas chromatography-mass analysis, the gas chromatography-infrared spectroscopy, the elementary analysis and the test using diethylamine.

Incidentally, in the gas chromatography, Model GC-8A supplied by Shimazu Seisakusho was used as the gas chromatograph, and capillary column FS-WCOT having a length of 25 m and a diameter of 0.25 mm, which was coated with silicone OV-215 supplied by Gasukuro Kogyo, was used as the column. The column temperature was adjusted to 27° C., 35° C. and 65° C. when tripropylamine, tributylamine and tripentylamine were used, respectively, as the starting organic compound.

Then, the fluorination of the electrochemical fluorination product with a fluorine gas was carried out by using a reaction vessel of nickel having an inner diameter of 5 cm and a height of 25 cm, which was provided with a stirrer and a reflux cooler ($-50°$ C.) arranged in the upper portion. A gas composed solely of fluorine or a gas composed of a mixture of fluorine and nitrogen was blown into the reaction vessel from the lower portion under conditions shown in Table 1. The reaction temperature was adjusted by using an oil bath. Hydrogen fluoride formed by the reaction was removed by neutralization, and then, the fluorination product was recovered. The amount of the fluorination product and the analysis results are shown in Table 1. In each run, an incompletely fluorinated product was not contained in the recovered fluorination product at all. At the run using tripentylamine, distillation was further conducted and 223 g of perfluorotripentylamine (having a purity of 95%) was obtained.

TABLE 1

Electrolytic Fluorination

| | | Electrolysis Conditions | | | | Product Composition*[1] | | | |
| --- | --- | --- | --- | --- | --- | --- | --- | --- | --- |
| | | | | | | | Amount(g) of Other Completely | Partially Fluorinated | |
| Run No. | Starting Material | Current Density ($A/dm^2$) | Voltage (V) | Temperature (°C.) | Electricity-Applying Time (Hr) | Amount Obtained (g) | Amount(g)[A] of Perfluoro Organic Compound Corresponding to Starting Material | Fluorinated Organic Compound | Amount Obtained (g) | F/H Ratio*[2] |
| 1 | tripropylamine | 3.5 | About 5.7 | 10 | 47 | 343 | 137 (25)*[3] | 86 | 120 | 9.1 |
| 2 | tributylamine | 3.0 | About 5.4 | 15 | 54 | 433 | 169 (30) | 121 | 143 | 13.0 |
| 3 | tripentylamine | 2.0 | About 5.2 | 5 | 78 | 350 | 141 (26) | 86 | 123 | 12.0 |

Fluorination with Fluorine Gas

| | | Reaction Conditions | | | | | Composition | | |
| --- | --- | --- | --- | --- | --- | --- | --- | --- | --- |
| Run No. | Starting Material | $F_2$ Feed Rate (ml/min) (room temperature) | $N_2F_2$ Mole Ratio | Temperature (°C.) | Time (Hr) | Amount Recovered (g) | Amount (a) [B] of Perfluoro Organic Compound Corresponding to Starting Material | Other Completely Fluorinated Organic Compound | [B]/[A] × 100 (%) |
| 1 | tripropylamine | 37 | 2 | 120 | 15 | 327 | 162 (29)*[3] | 165 | 118 |
| 2 | tributylamine | 45 | 0 | 130 | 10 | 403 | 255 (46) | 148 | 151 |
| 3 | tripentylamine | 80 | 4 | 150 | 4 | 316 | 216 (40) | 100 | 153 |

Note
*[1] determined by (amount obtained or recovered) × (area ratio of each component in gas chromatogram).
*[2] with respect to each peak of the partially fluorinated compound in the gas chromatogram, the area ratio was determined and the composition formula was determined, and the ratio of the number of fluorine atoms to the number of hydrogen atoms (F/H ratio) in the partially fluorinated organic compound as a whole was calculated.
*[3] each parenthesized value indicates the yield (%) based on the starting material.

EXAMPLE 2

The electrochemical fluorination was carried out in the same manner as adopted at Run No. 3 of Example 1 by using partially fluorinated tripentylamine having an F/H ratio 1/5, and the obtained fluorination product was subjected to rectification to obtain 192 g of an electrochemical fluorination product containing a partially fluorinated organic compound having an F/H ratio of 13.2. The composition of the obtained electrochemical fluorination product is shown in Table 2. The fluorination of the electrochemical fluorination product with a fluorine gas was carried out in the same manner as adopted at Run No. 3 of Example 1. The amount and composition of the fluorination product recovered after the reaction and the increased amount of perfluorotripentylamine are shown in Table 2. Incidentally, an incompletely fluorinated compound was not observed in the product obtained by the fluorination with the fluorine gas at all.

Table 3 were carried out by using the apparatus described in Example 1 according to the same procedures as described in Example 1.

Incidentally, the fluorine gas fluorination was carried out in the liquid phase under an elevated pressure.

The reaction conditions, the amount of the obtained

TABLE 2

| | Electrolytic Fluorination Product | | | Product by Fluorination with Fluorine Gas | | | |
|---|---|---|---|---|---|---|---|
| | Composition (g) | | | | Composition (g) | | |
| | Amount (g) | Partially Fluorinated Organic Compound | Perfluorotri-pentylamine | Other Completely Fluorinated Compound | Amount (g) | Perfluorotri-pentylamine | Other Completely Fluorinated Compound | Increased Amount (g) of Perfluorotri-pentylamine |
| Example 2 | 192 | 124.5 | 60.5 | 7.0 | 176 | 111.5 | 64.5 | 51 |

EXAMPLE 3

The electrolytic fluorination and subsequent fluorine gas fluorination of three organic compounds shown in Table 3 were carried out... fluorination product, the amount of the target perfluoro organic compound and the presence or absence of an incompletely fluorinated compound are shown in Table 3.

TABLE 3

| | Electrolytic Fluorination | | | |
|---|---|---|---|---|
| | Electrolysis Conditions *1 | | | |
| Starting Material | Current Density (A/dm$^2$) | Voltage (V) | Electrocity-Applying Time (Hr) | Amount Obtained (g) |
| $CH_3(CH_2)_4COCl$*2 150 g | 2 | About 5.7 | 53 | 315 |
| $CH_3(CH_2)_7SO_2Cl$ 150 g | 2 | About 5.8 | 51 | 243 |
| (tetrahydropyran ring: $CH_2-CH_2$ / $CH_2$ \ O / $CH_2-CH_2$) 150 g | 2 | About 5.1 | 65 | 327 |

| | Electrolytic Fluorination | | | |
|---|---|---|---|---|
| | Product | | | |
| | Perfluoro Organic Compound Corresponding to Starting Material | | Partially Flourinated Organic Compound | |
| Starting Material | Structure | Amount (g)[A] | Amount (g) | F/H (Ratio) |
| $CH_3(CH_2)_4COCl$*2 150 g | $C_5F_{11}COF$ | 55 (16)*3 | 47 | 10.3 |
| | $C_6F_{12}O$ | 106 (30) | | |
| $CH_3(CH_2)_7SO_2Cl$ 150 g | $C_8F_{17}SO_2F$ | 108 (31) | 31 | 10.9 |
| (tetrahydropyran ring) | $CF_2-CF_2$ / $CF_2$ \ O / $CF_2-CF_2$ | 169 | 46 | 9.0 |

| | Fluorination with Fluorine Gas | | | |
|---|---|---|---|---|
| | Reaction conditons | | | |
| Starting Material | F$_2$ Feed Rate (ml/min) (room temperature, atmospheric Pressure) | N$_2$/F$_2$ Mole Ratio | Temperature (°C.) | Time (Hr) |
| $CH_3(CH_2)_4COCl$*2 150 g | 10 | 3 | 120 | 20 |
| $CH_3(CH)_7SO_2Cl$ 150 g | 20 | 3 | 125 | 10 |
| (tetrahydropyran ring) 150 g | 30 | 3 | 115 | 10 |

| Fluorination with Fluorine Gas |
|---|
| Product |
| Perfluoro Organic Compound    Incompletely |

TABLE 3-continued

| Starting Material | Recovered Amount (g) | Corresponding to Starting Material Structure | Amount (g) B | Fluorinated Product | [B]/[A] × 100(%) |
|---|---|---|---|---|---|
| $CH_3(CH_2)_4COCl$*2 150 g | 300 | $C_5F_{11}COF$ | 63 (18)*3 | Absent | 115 |
|  |  | $C_6F_{12}O$ | 121 (34) |  | 114 |
| $CH_3(CH_2)_7SO_2Cl$ 150 g | 235 | $C_8F_{17}SO_2F$ | 129 (37) | Absent | 119 |
| 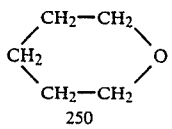 250 | 307 | 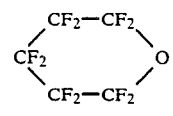 | 186 (40) | Absent | 110 |

Note
*1 the amount used of anhydrous hydrogen fluoride was 1000 g and the electrolysis temperature was 0° C.
*2 in case of $C_5H_{11}COCl$, the electrochemical fluorination product was directly fluorinated with $F_2$ without neutralization of hydrogen fluoride.
*3 each parenthesized value indicates the yield (%) based on the starting material.

EXAMPLE 4

Four trialkylamines were fluorinated with cobalt trifluoride. More specifically, a reactor of nickel having a length of 110 cm and an inner diameter of cm, which was provided with a stirrer, was charged with 3.7 kg of cobalt trifluoride, and a gasified trialkylamine was supplied together with a nitrogen gas into the reactor from the end thereof. The reaction product and hydrogen fluoride flowing out from the reactor were condensed by a cooling trap to separate them from the nitrogen gas. The reaction conditions are shown in Table 4. After the reaction, only the nitrogen gas was caused to flow through the reactor for 2 hours to recover the product contained in the reactor. The reaction product comprising hydrogen fluoride and the fluorination product was washed with an alkaline aqueous solution and water and was then dehydrated and subjected to distillation to separate and remove high-boiling-point compounds. The amount and composition of the so-obtained fluorination product are shown in Table 4. The analysis was carried out in the same manner as described in Example 1. Incidentally, in the gas chromatography, the column temperature was 27° C., 65° C. and 125° C. in case of tripropylamine, tripentylamine and trioctylamine, respectively.

Then, fluorination with a fluorine gas was carried out in the following manner.

A reactor of nickel having an inner diameter of 3 cm and a height of 25 cm, which was provided with a reflux cooler (−50° C.), was filled with a Rasching ring composed of nickel, and a gaseous mixture of fluorine and nitrogen was blown into the reactor from the lower portion thereof under conditions shown in Table 4. The reaction temperature was adjusted by using an oil bath. Hydrogen fluoride formed by the reaction was neutralized and removed, and the fluorination product was recovered. The amount of the obtained fluorination product and the analysis results are shown in Table 4. In each case, an incompletely fluorinated compound was not contained in the fluorination product at all. Incidentally, in case of tripentylamine, distillation was further conducted to obtain 31 g of perfluorotripentylamine having a purity of 96%.

TABLE 4

Fluorination with Cobalt Trifluoride

| | | | Reaction Conditions | | | Product Composition*1 | | | |
|---|---|---|---|---|---|---|---|---|---|
| | Starting Material | | Flow Rate (g/Hr) of | Flow Rate (ml/min) | | | Amount (g) [A] of Perfluoroalkylamine Corresponding | Amount (g) of Other | Partially Fluorinated Trialkylamine | |
| Run No. | Kind | Amount (g) | Starting Material | of Nitrogen Gas | Temperature (°C.) | Obtained Amount (g) | to Starting Material | Perfluoro Compound | Amount (g) | F/H Ratio*2 |
| 1 | Tripropylamine $N(C_3H_7)_3$ | 40 | 8 | 30 | 230 | 70.7 | 29.8 (20)*3 | 26.2 | 14.7 | 12.2 |
| 2 | Tributylamine $N(C_4H_9)_3$ | 40 | 7.5 | 40 | 230 | 58.6 | 25.8 (17) | 17.1 | 15.7 | 13.2 |
| 3 | Tripentylamine $N(C_5H_{11})_3$ | 35 | 5.4 | 70 | 260 | 51.2 | 21.0 (17) | 18.5 | 11.7 | 11.5 |
| 4 | Trioctylamine $N(C_8H_{17})_3$ | 35 | 4.7 | 100 | 280 | 49.0 | 20.2 (16) | 14.6 | 14.2 | 10.5 |

Fluorination with Fluorine Gas

| | Reaction Conditions | | | | | Product Composition*1 | | |
|---|---|---|---|---|---|---|---|---|
| Run No. | $F_2$ Feed Rate (ml/min) (room temperature) | $N_2/F_2$ Mole Ratio | Temperature (°C.) | Time (Hr) | Recovered Amount (g) | Amount (g) [B] of Perfluorotrialkylamine Corresponding to Starting Material | Amount (g) of Other Perfluoro Compound | (B)/(A) × 100 (%) |
| 1 | 6 | 2 | 140 | 12 | 66.7 | 38.4 (26)*3 | 28.3 | 129 |
| 2 | 8 | 2 | 140 | 8 | 56.8 | 37.7 (25) | 19.1 | 146 |

TABLE 4-continued

| | | | | | | | | |
|---|---|---|---|---|---|---|---|---|
| 3 | 6 | 2 | 145 | 12 | 47.2 | 30.5 (24) | 16.7 | 145 |
| 4 | 8 | 2 | 145 | 8 | 45.3 | 25.9 (21) | 19.4 | 128 |

Note
*[1](amount of obtained or recovered product) × (area ratio of each product in gas chromatogram)
*[2]with respect to each peak of the partially fluorinated trialkylamine in the gas chromatogram, the area ratio was determined and the composition formula was determined, and the ratio of the number of fluorine atoms to the number of hydrogen atoms (F/H ratio) in the partially fluorinated trialkylamine as a whole was calculated.
*[3]each parenthesized value indicates the yield (%) based on the starting material.

COMPARATIVE EXAMPLES 1 AND 2

The fluorination of tributylamine as the starting material with cobalt trifluoride and the post treatment were carried out in the same manner as described in Example 4. The fluorination of the obtained product with a fluorine gas was carried out in the same manner as described in Example 4 except that the reaction temperature was changed to 100° or 190° C. Hydrogen fluoride was neutralized and removed, and the fluorination product was recovered and analyzed. The obtained results are shown in Table 5.

In Table 5, the value of [B]/[A]×100 is almost 100. From this fact, it is seen that the fluorination with a fluorine gas was not substantially effective in these runs.

TABLE 6

| | Fluorination with Potassium Tetrafluorocobate | | | | Fluorination with Fluorine Gas | | | | |
|---|---|---|---|---|---|---|---|---|---|
| | | Composition | | | | Composition | | | |
| | Amount (g) | Amount (g) (A) of perfluorotripentylamine | Amount (g) of Other Perfluoro Compound | Amount (g) of Partially Fluorinated Tripentylamine | Recovered Amount (g) | Amount (g) (B) of Perfluorotripentylamine | Amount (g) of Other Perfluoro Compound | Incompletely Fluorinated Compound | (B)-(A) (g) |
| I | 18.0 | 5.3 | 0.9 | 11.8 | 17.5 | 9.8 | 7.7 | not detected | 4.5 |
| II | 38.0 | 25.3 | 0.9 | 11.8 | 36.4 | 34.6 | 1.8 | not detected | 9.3 |

3 of Example 4, and hydrogen fluoride was neutralized. The obtained results are shown in Table 6.

EXAMPLE 6

Electrochemical fluorination of tripentylamine was carried out in the same manner at Run No. 3 of Example 1 to obtain 353 g of a fluorination product which comprised 140 g (yield=26%) of perfluorotripentylamine, 88 g of other completely fluorinated organic compound and 125 g of partially fluorinated organic compound having an F/H ratio of 13.3.

The fluorination of the electrochemical fluorination product with a fluorine gas was carried out by using a reactor of nickel having an inner diameter of 1 cm and a length of 60 cm, which had a reflux cooler in the upper portion thereof and was filled with nickel parti-

TABLE 5

| | Product by Fluorination with Cobalt Trifluoride | | | | |
|---|---|---|---|---|---|
| | | Amount (g) | Composition | | |
| Comparative Example No. | Obtained Amount (g) | [A] of Perfluorotributylamine | Amount (g) of Other Perfluoro Compound | Partially Fluorinated Tributylamine | |
| | | | | (g) | F/H Ratio |
| 1 | 58.2 | 25.3 | 17.5 | 15.4 | 13.0 |
| 2 | 58.1 | 25.4 | 17.6 | 15.1 | 12.0 |

| | | | Partially Fluorinated Tributylamine | | | |
|---|---|---|---|---|---|---|
| | | | Composition | | | |
| Comparative Example No. | Reaction Temperature (°C.) | Recovered Amount (g) | Amount (g) [B] of Perfluorotributylamine | Amount (g) of Other Perfluoro Compound | Amount (g) of Incompletely Fluorinated Compound | [B]/[A] × 100 (%) |
| 1 | 100 | 56.4 | 25.8 | 15.5 | 15.1 | 102 |
| 2 | 190 | 53.9 | 24.8 | 29.1 | not detected | 98 |

EXAMPLE 5

Tripentylamine was fluorinated in the same manner as at Run No. 3 of Example 4 except that potassium tetrafluorocobaltate was used instead of cobalt trifluoride. The obtained fluorination product was subjected to rectification to obtain a product comprising a partially fluorinated trialkylamine having an F/H ratio of 10.0 as the main component (64% by weight). The fluorination of 18.0 g of the so-obtained product (I) or a mixture of 18 g of the so-obtained product and 20 g of perfluorotripentylamine (11) with a fluorine gas was carried out at 145° C. in the same manner as at Run No.

cles. The electrochemical fluorination product was supplied at a rate of 8 g/hour from the head of the reactor and the fluorine gas was supplied at a rate of 4 ml/min from the lower portion of the reactor. A nitrogen gas was supplied at a rate of 6 ml/min at a point apart by ⅓ of the total length from the lower end of the reactor and at a rate of 12 ml at a point apart by ⅓ of the total length of the reactor from the upper end. The temperature at the upper end of the reactor was 120° C., and the temperature was gradually elevated toward the lower end of the reactor (150° C.). The residence time of the reaction liquid in the reactor was 5 hours. The fluorination product collected from the lower portion of the reactor was subjected to a neutralization treatment and was then recovered. The amount of the recovered product was 320 g, and the recovered product comprised 253 g (yield=47%) of perfluorotripentylamine and 67 g of other completely fluorinated organic compound. Any incompletely fluorinated compound was not detected.

COMPARATIVE EXAMPLE 3

Tripentylamine was fluorinated in the gas phase with cobalt trifluoride to obtain partially fluorinated tripentylamine having an F/H ratio of 3.1. Then, 175 g of this partially fluorinated tripentylamine was fluorinated with a fluorine gas in the same manner as at Run No. 3 of Example 1 except that the fluorine gas feed rate was adjusted to 100 ml/min and the reaction time was changed to 40 hours. After the passage of 10, 20 and 30 hours from the start of the reaction and after termination of the reaction, the reaction liquid was sampled and analyzed. In each case, the product by the fluorination with the fluorine gas was composed of decomposition products, and perfluorotripentylamine was not substantially contained.

COMPARATIVE EXAMPLE 4

The procedures of Run No. 3 of Example 1 were repeated in the same manner except that the electrolytic fluorination of 150 g of tripentylamine was carried out at a temperature of $-5°$ C. and a current density of 3 A/dm$^2$ for an electricity-applying time of 52 hours and the voltage was 5.9 V. Hydrogen fluoride contained in the product deposited in the bottom portion of the electrolytic cell was neutralized and removed, and the product was washed with water and dried to obtain 345 g of a fluorination product comprising 140 g of perfluorotripentylamine, 89 g of other completely fluorinated compound and 116 g of a partially fluorinated organic compound having an F/H ratio of 19/1. Namely, the content of the partially fluorinated compound was about 33.6% by weight.

COMPARATIVE EXAMPLE 5

Fluorination of 50 g of tripropylamine with a fluorine gas was carried out by using the reaction vessel described in Example 1. The reaction temperature was adjusted to 120° C. Fluorine gas and nitrogen gas were supplied at rates of 100 ml/min and 200 ml/min, respectively, for 50 hours. The obtained fluorination product was composed of a perfluorinated decomposition product, and perfluorotripropylamine was not substantially contained.

Then, the reaction temperature was changed to $-15°$ C., and the fluorination of tripropylamine was carried out by supplying fluorine gas and nitrogen gas at flow rates of 25 ml/min and 225 ml/min, respectively, for 200 hours. The fluorination product was composed mainly of perfluorinated decomposition products such as nitrogen trifluoride and carbon tetrafluoride, and 10.2 g (yield=6%) of perfluorotripropylamine and 22.3 g of an incompletely fluorinated organic compound were contained.

We claim:

1. A process for the preparation of a perfluoro organic compound by perfluorination of an organic compound having carbon-to-hydrogen bonds, which consists essentially of:
   (i) a first step of fluorinating an organic compound having carbon-to-hydrogen bonds by contact with at least one metal fluoride selected from the group consisting of cobalt trifluoride, potassium tetrafluorocobaltate, silver difluoride and manganese trifluoride to form a mixture of a perfluoro organic compound with partially fluorinated, organic compounds in which the ratio of the number of fluorine atoms to the number of hydrogen atoms is at least 8; and
   (ii) a second step of contacting substantially all of said mixture formed in said first step with molecular fluorine at a temperature of 110° to 180° C. to convert said partially fluorinated organic compounds to a perfluoro organic compound as product and recovering said perfluoro organic compound.

* * * * *